United States Patent
Burckbuchler et al.

(10) Patent No.: US 11,504,317 B2
(45) Date of Patent: Nov. 22, 2022

(54) PROCESS FOR CURL-RELAXING AND/OR STRAIGHTENING KERATIN FIBRES, USING REDUCING AGENTS AND POLAR ORGANIC SOLVENTS, AND STRAIGHTENING KIT

(71) Applicant: L'OREAL, Paris (FR)

(72) Inventors: Virginie Burckbuchler, Aulnay-sous-Bois (FR); Henri Samain, Bievres (FR)

( * ) Notice: Subject to any disclaimer, the term of this patent is extended or adjusted under 35 U.S.C. 154(b) by 173 days.

(21) Appl. No.: 16/473,218

(22) PCT Filed: Dec. 22, 2017

(86) PCT No.: PCT/EP2017/084296
§ 371 (c)(1),
(2) Date: Jun. 24, 2019

(87) PCT Pub. No.: WO2018/115392
PCT Pub. Date: Jun. 28, 2018

(65) Prior Publication Data
US 2019/0350830 A1    Nov. 21, 2019

(30) Foreign Application Priority Data
Dec. 22, 2016  (FR) ...................................... 1663190

(51) Int. Cl.
| | |
|---|---|
| *A61Q 5/04* | (2006.01) |
| *A61K 8/46* | (2006.01) |
| *A45D 7/06* | (2006.01) |
| *A61K 8/34* | (2006.01) |
| *A61K 8/37* | (2006.01) |
| *A45D 7/00* | (2006.01) |

(52) U.S. Cl.
CPC .................. *A61K 8/46* (2013.01); *A45D 7/06* (2013.01); *A61K 8/345* (2013.01); *A61K 8/347* (2013.01); *A61K 8/37* (2013.01); *A61Q 5/04* (2013.01); *A45D 2007/002* (2013.01); *A45D 2200/15* (2013.01); *A45D 2200/25* (2013.01); *A61K 2800/884* (2013.01)

(58) Field of Classification Search
None
See application file for complete search history.

(56) References Cited

U.S. PATENT DOCUMENTS

| | | | | |
|---|---|---|---|---|
| 5,609,860 | A  * | 3/1997 | Tabata | A61K 8/23 424/70.5 |
| 2012/0192888 | A1* | 8/2012 | Philippe | A61K 8/42 132/206 |
| 2016/0058683 | A1* | 3/2016 | Engrassi | A61K 8/36 132/206 |

\* cited by examiner

*Primary Examiner* — Jyothsna A Venkat
(74) *Attorney, Agent, or Firm* — Christensen O'Connor Johnson Kindness PLLC

(57) ABSTRACT

The present invention relates to a process for curl-relaxing and/or straightening keratin fibres, such as the hair, which comprises the application to the fibres of one or more compositions comprising reducing agents, one or more compositions comprising organic solvents and a step of heat treatment of the fibres by means of a heating tool. The invention also relates to the use of the composition(s) comprising reducing agents and of the composition(s) comprising organic solvents in a process for curl-relaxing and/or straightening keratin fibres. Finally, the invention relates to a multi-compartment device or "kit" that is suitable for performing such a process.

1 Claim, 1 Drawing Sheet

… …

PROCESS FOR CURL-RELAXING AND/OR STRAIGHTENING KERATIN FIBRES, USING REDUCING AGENTS AND POLAR ORGANIC SOLVENTS, AND STRAIGHTENING KIT

The present invention relates to a process for curl-relaxing and/or straightening keratin fibres, such as the hair, which comprises the application to the fibres of one or more compositions comprising reducing agents, one or more compositions comprising polar organic solvents and a step of heat treatment of the fibres by means of a heating tool.

The invention also relates to the use of the composition(s) comprising reducing agents and of the composition(s) comprising organic solvents in a process for curl-relaxing and/or straightening keratin fibres.

Finally, the invention relates to a multi-compartment device or "kit" that is suitable for performing such a process.

Many people are not satisfied with the appearance of their hair. In particular, people who have curly hair usually seek to obtain straight hair.

To obtain permanent reshaping of the hair such as straightening of the hair, uncurling or relaxing of the curls, the technique most commonly used consists, in a first stage, in opening the —S—S— disulfide bonds of keratin (keratocystine) generally by means of a basic composition containing a sulfur-based reducing agent (reduction step), and then, after having rinsed the head of hair thus treated, generally with water, in reconstituting, in a second stage, said disulfide bonds by applying to the hair, which has been placed under tension beforehand, an oxidizing composition (oxidation step, also known as the fixing step) so as finally to give the hair the desired shape.

The new shape given to the hair by such a chemical treatment is eminently long-lasting and especially withstands washing with water or shampoos, as opposed to the simple standard techniques of temporary reshaping, such as hairsetting.

Many products intended for straightening or uncurling the hair or for curl relaxing exist on the market.

The products intended for straightening or uncurling are generally formulated either using very alkaline compositions, with a pH above 12, or using a high concentration of thiols, such as mercaptan compounds.

The oxidizing compositions required for performing the fixing step are usually compositions based on aqueous hydrogen peroxide solution.

However, the application of these products is generally long, with a longer or shorter leave-on time depending on the product, the type of hair and the desired effect. It requires precise know-how, which is mainly due to the high contents of reducing agents used in the reducing compositions or to the high contents of hydroxides and/or to the very alkaline pH of the relaxing compositions, and also to the various longer or shorter leave-on times of these compositions.

It has also been found that the use of these reducing agents or of these strong alkaline agents can lead to scalp discomfort (irritation, itching, etc.).

Moreover, the compositions employed often pose problems of odours, in particular the reducing compositions and especially those containing thiols. Hair treated with these compositions may also retain an unpleasant odour.

Furthermore, the reducing agents are generally used in high concentrations, which may lead to more or less pronounced degradation of the keratin fibre, in particular when the hair is dyed.

These techniques can thus bring about, in the long term, impairment of the quality of the hair, leading to a decrease in its cosmetic properties, such as its vitality or its sheen, and a degradation in its mechanical properties, more particularly in its mechanical strength.

The impact of these treatments on the quality of the head of hair is poorly tolerated by users, who then have a tendency to abandon their treatments or to perform them at long intervals.

Furthermore, the use of a curl-relaxing treatment is especially intricate if the quality of the hair comprises disparities along the fibre, as in the case of damaged ends (which occurs in particular in the case of long hair) or in the case of bleached parts of the hair (which occurs in particular in highlighted hair).

One possibility is to use compositions containing more or less concentrated thiols on the different parts of the head of hair as a function of its state, which would necessitate lock-by-lock manipulation. However, the application of a thiol-based composition is unpleasant for the operator (typically the hair stylist), who then has a tendency to go faster during this application, and does not wish to perform these lock-by-lock manipulations.

Another possibility is to apply a single thiol formulation to the head of hair and then to treat the locks with the heating tool while limiting the contact of the tool with the embrittled areas of the fibres, or while reducing the temperature of said tool. However, this solution is not satisfactory either, since the embrittled parts of the hair, which will have been manipulated with the heating to for a reduced contact time or at a reduced temperature, will be sparingly treated and will return to curling before the other hair.

Thus, a process is sought that can be used in the case of heterogeneous hair, making it possible to relax the curls and giving an equivalent straightening effect irrespective of the initial state of the keratin fibre.

The term "heterogeneous hair" means hair comprising, along the keratin fibres of the hair, embrittled and/or damaged areas, and dry, coarse, brittle or split areas.

In parallel, this process must retain good performance qualities in terms of the straightening of keratin fibres, in particular with an effect that is persistent on shampooing several times.

Furthermore, it is desirable for these treatments to be easy to apply, and comfortable for the operator to use, in particular in terms of odours deriving from the use of such a process.

The Applicant has now discovered that the use of a particular process in at least three steps makes it possible to meet the abovementioned objectives.

It has thus discovered, surprisingly, a process for curl-relaxing and/or straightening keratin fibres, in particular human keratin fibres such as the hair, in several steps, which comprises:

i) the application to said fibres of an acidic composition (A), preferably having a pH between 1 and 5 inclusive and containing one or more thiol-based reducing agents;

ii) the application to said fibres of a distinct composition (B) containing one or more polar organic solvents; followed by iii) a step of heat treatment of the fibres by means of a heating tool; it being understood that steps i) and ii) are performed separately i) then ii) or else ii) then i). Preferably, the steps of the process are performed in the following order: i) then ii) then iii). This process makes it possible to achieve the desired properties, inter alia in terms of integrity, quality and cosmeticity of the keratin fibres, while at the same time obtaining curl relaxation and/or straightening of keratin fibres that is of good quality and long-lasting in particular on embrittled hair.

One subject of the present invention is thus a process for curl-relaxing and/or straightening keratin fibres, in particular keratin fibres such as the hair, comprising steps i), ii) and iii) as defined previously.

The implementation of this process makes it possible to obtain curl relaxation and/or straightening of keratin fibres that is of good quality and persistent on shampooing several times while preserving the quality and integrity of the keratin fibres. Furthermore, the implementation of this process makes it possible to provide the keratin fibres with good cosmetic properties, in particular sheen and a soft feel.

In a preferred variant, the process according to the invention is a process for straightening keratin fibres, in particular the hair.

A subject of the invention is also a kit that is suitable for performing the process of the invention. This kit comprises at least two compartments:
 a first compartment comprising an acidic composition (A), preferably at a pH between 1 and 5 inclusive, which comprises one or more thiol-based reducing agents;
 a second compartment comprising a composition (B) which comprises one or more polar organic solvents and
 optionally, a third compartment comprising a composition (C) which comprises one or more non-thiol-based reducing agents.

A subject of the present invention is also a composition (A) that is suitable for performing the process of the invention. This cosmetic composition comprises one or more thiol-based reducing agents, and is acidic at a pH between 1 and 5 inclusive, preferably between 2.5 and 4.

The term "pH between 1 and 5 inclusive" means that the limits 1 and 5 are included in the pH range.

A subject of the present invention is also the use of compositions (A) and (B) in a process for shaping, curl-relaxing and/or straightening keratin fibres, especially human keratin fibres such as the hair.

Such a process is rapid and simple to perform, and does not require any particular know-how.

Furthermore, performing this process makes it possible to obtain curl relaxation and/or a reduction of the volume of the head of hair that is gradual. By virtue of its protection of the integrity of keratin fibres, the implementation of this process makes it possible to give them good cosmetic properties, in particular sheen and a soft feel.

In particular, it is possible to modulate the desired effect, by successively performing such a process.

Finally, the process according to the invention makes it possible to substantially reduce the unpleasant odours derived from performing a standard curl relaxation and/or straightening process.

Other characteristics and advantages of the invention will emerge more clearly on reading the description, the examples and the figures that follow.

SINGLE FIGURE

The single FIGURE shows on the left, a lock of hair treated according to a process of the invention (the composition containing one or more thiol-based reducing agents having a pH=3.51).

The single FIGURE shows on the right, a lock of hair treated according to a comparative process (the composition containing one or more thiol-based reducing agents having a pH=8.52).

For the purposes of the present invention and unless otherwise indicated:

the term "(hetero)aryl" means aryl and heteroaryl groups;

the "aryl" or "heteroaryl" radicals or the aryl or heteroaryl part of a radical may be substituted with at least one substituent borne by a carbon atom, chosen from:
 a $C_1$-$C_6$ and preferably $C_1$-$C_4$ alkyl radical optionally substituted with one or more radicals chosen from hydroxyl, $C_1$-$C_2$ alkoxy, $C_2$-$C_4$ (poly)hydroxyalkoxy, acylamino, amino substituted with two $C_1$-$C_4$ alkyl radicals, which may be identical or different, optionally bearing at least one hydroxyl group, or the two radicals possibly forming, with the nitrogen atom to which they are attached, a saturated or unsaturated, optionally substituted 5- to 7-membered and preferably 5- or 6-membered heterocycle optionally comprising another nitrogen or non-nitrogen heteroatom;
 a halogen atom;
 a hydroxyl or thiol group;
 a $C_1$-$C_6$ alkoxy or $C_1$-$C6$ alkylthio radical;
 a (poly)hydroxy($C_2$-$C_6$)alkoxy radical;
 an amino radical;
 a 5- or 6-membered heterocycloalkyl radical, preferentially morpholino, piperazino, piperidino or pyrolidino, which is optionally substituted with a ($C_1$-$C_4$) alkyl radical, preferentially methyl;
 a 5- or 6-membered heteroaryl radical, preferentially imidazolyl, optionally substituted with a ($C_1$-$C_4$)alkyl radical, preferentially methyl;
 an amino radical substituted with one or two identical or different $C_1$-$C_6$ alkyl radicals, optionally bearing at least:
  i) a hydroxyl group,
  ii) an amino group optionally substituted with one or two optionally substituted $C_1$-$C_3$ alkyl radicals, said alkyl radicals possibly forming with the nitrogen atom to which they are attached a saturated or unsaturated, optionally substituted 5- to 7-membered heterocycle, optionally comprising at least one other nitrogen or non-nitrogen heteroatom,
  iii) a quaternary ammonium group —$N^+R'R''R'''$, $M^-$ for which R', R" and R''', which may be identical or different, represent a hydrogen atom or a $C_1$-$C_4$ alkyl group and $M^-$ represents an anionic counterion,
  iv) or an optionally cationic 5- or 6-membered heteroaryl radical, preferentially imidazolium, optionally substituted with a ($C_1$-$C_4$)alkyl radical, preferentially methyl;
 an acylamino radical (—N(R)—C(O)—R') in which the R radical is a hydrogen atom or a $C_1$-$C_4$ alkyl radical optionally bearing at least one hydroxyl group and the $R^1$ radical is a $C_1$-$C_2$ alkyl radical;
 a carbamoyl radical (($R)_2$N—C(O)—) in which the R radicals, which may be identical or different, represent a hydrogen atom or a $C_1$-$C_4$ alkyl radical optionally bearing at least one hydroxyl group;
 an alkylsulfonylamino radical (R'—S(O)$_2$—N(R)—) in which the R radical represents a hydrogen atom or a $C_1$-$C_4$ alkyl radical optionally bearing at least one hydroxyl group and the R' radical represents a $C_1$-$C_4$ alkyl radical, or a phenyl radical;
 an amino sulfonyl radical (($R)_2$N—S(O)$_2$—) in which the R radicals, which may be identical or different, represent a hydrogen atom or a $C_1$-$C_4$ alkyl radical optionally bearing at least one hydroxyl group;

a carboxyl radical in the acid or salified form (preferably salified with an alkali metal or a substituted or unsubstituted ammonium);

a cyano group;

a nitro or nitroso group;

a polyhaloalkyl group, preferably trifluoromethyl;

the cyclic or heterocyclic part of a non-aromatic radical may be substituted with at least one substituent chosen from the following groups:

hydroxyl;

$C_1$-$C_4$ alkoxy, $C_2$-$C_4$ (poly)hydroxyalkoxy;

$C_1$-$C_4$ alkyl;

alkylcarbonylamino (R—C(O)—N(R')—) in which the radical R' is a hydrogen atom or a $C_1$-$C_4$ alkyl radical optionally bearing at least one hydroxyl group, and the radical R is a $C_1$-$C_2$ alkyl radical or an amino radical optionally substituted with one or two $C_1$-$C_4$ alkyl groups, which may be identical or different, themselves optionally bearing at least one hydroxyl group, said alkyl radicals possibly forming, with the nitrogen atom to which they are attached, a saturated or unsaturated, optionally substituted 5- to 7-membered heterocycle optionally comprising at least one other nitrogen or non-nitrogen heteroatom;

alkylcarbonyloxy (R—C(O)—O—) in which the radical R is a $C_1$-$C_4$ alkyl radical or an amino group optionally substituted with one or two identical or different $C_1$-$C_4$ alkyl groups themselves optionally bearing at least one hydroxyl group, said alkyl radicals possibly forming with the nitrogen atom to which they are attached a saturated or unsaturated, optionally substituted 5- to 7-membered heterocycle, optionally comprising at least one other nitrogen or non-nitrogen heteroatom;

alkoxycarbonyl (R—X—C(O)—) in which the radical R is a $C_1$-$C_4$ alkoxy radical, X is an oxygen atom or an amino group optionally substituted with a $C_1$-$C_4$ alkyl group itself optionally bearing at least one hydroxyl group, said alkyl radical possibly forming with the nitrogen atom to which it is attached a saturated or unsaturated, optionally substituted 5- to 7-membered heterocycle, optionally comprising at least one other nitrogen or non-nitrogen heteroatom;

a cyclic or heterocyclic radical, or a non-aromatic part of an aryl or heteroaryl radical, may also be substituted with one or more oxo groups;

a hydrocarbon-based chain is unsaturated when it comprises one or more double bonds and/or one or more triple bonds;

an "aryl" radical represents a monocyclic or fused or non-fused polycyclic carbon-based group, comprising from 6 to 22 carbon atoms, at least one ring of which is aromatic; preferentially, the aryl radical is a phenyl, biphenyl, naphthyl, indenyl, anthracenyl or tetrahydronaphthyl;

a "heteroaryl radical" represents a fused or non-fused, optionally cationic, 5- to 22-membered monocyclic or polycyclic group, comprising from 1 to 6 heteroatoms chosen from nitrogen, oxygen, sulfur and selenium atoms, and at least one ring of which is aromatic; preferentially, a heteroaryl radical is chosen from acridinyl, benzimidazolyl, benzobistriazolyl, benzopyrazolyl, benzopyridazinyl, benzoquinolyl, benzothiazolyl, benzotriazolyl, benzoxazolyl, pyridyl, tetrazolyl, dihydrothiazolyl, imidazopyridyl, imidazolyl, indolyl, isoquinolyl, naphthoimidazolyl, naphthooxazolyl, naphthopyrazolyl, oxadiazolyl, oxazolyl, oxazolopyridyl, phenazinyl, phenoxazolyl, pyrazinyl, pyrazolyl, pyrilyl, pyrazoyltriazyl, pyridyl, pyridinoimidazolyl, pyrrolyl, quinolyl, tetrazolyl, thiadiazolyl, thiazolyl, thiazolopyridyl, thiazoylimidazolyl, thiopyrylyl, triazolyl, xanthinyl or thioxanthinyl;

a "heterocyclic radical" is a fused or non-fused, 5- to 22-membered monocyclic or polycyclic radical, possibly containing one or two unsaturations but non-aromatic, comprising from 1 to 6 heteroatoms chosen from nitrogen, oxygen, sulfur and selenium atoms;

an "alkyl" radical is a linear or branched, saturated $C_1$-$C_{10}$, in particular $C_1$-$C_8$, more particularly $C_1$-$C_6$ and preferably $C_1$-$C_4$, hydrocarbon-based radical;

an "alkoxy" radical is an "alkyl-oxy" radical in which the alkyl group is as defined previously;

an "alkenyl" radical is a linear or branched $C_2$-$C_{10}$, in particular $C_2$-$C_8$, more particularly $C_2$-$C_6$, preferably $C_2$-$C_4$, hydrocarbon-based radical comprising one or more conjugated or non-conjugated unsaturations, preferably comprising one or two double bonds, such as ethylenyl;

the expression "optionally substituted" attributed to the alkyl or alkenyl radical is intended to mean that said alkyl or alkenyl radical may be substituted with one or more radicals chosen from the following radicals: i) hydroxyl, ii) $C_1$-$C_4$ alkoxy, iii) acylamino, iv) amino optionally substituted with one or two identical or different $C_1$-$C_4$ alkyl radicals, said alkyl radicals possibly forming, with the nitrogen atom that bears them, a 5- to 7-membered heterocycle, optionally comprising another nitrogen or non-nitrogen heteroatom; v) carboxy; or vi) aryl such as phenyl optionally substituted with one or more (di)($C_1$-$C_4$)(alkyl)amino groups or hydroxyl groups;

an "alkoxy" radical is an alkyl-oxy radical for which the alkyl radical is a linear or branched $C_1$-$C_8$ and preferentially $C_1$-$C_6$ hydrocarbon-based radical;

when the alkoxy group is optionally substituted, this implies that the alkyl group is optionally substituted as defined above;

the term "organic or mineral acid salt" is more particularly intended to mean salts chosen from a salt derived from i) hydrochloric acid HCl, ii) hydrobromic acid HBr, iii) sulfuric acid $H_2SO_4$, iv) alkylsulfonic acids: Alk-S(O)$_2$OH such as methanesulfonic acid and ethanesulfonic acid; v) arylsulfonic acids: Ar—S(O)$_2$OH such as benzenesulfonic acid and toluenesulfonic acid; vi) citric acid; vii) succinic acid; viii) tartaric acid; ix) lactic acid; x) alkoxysulfinic acids: Alk-O—S(O)—OH such as methoxysulfinic acid and ethoxysulfinic acid; xi) aryloxysulfinic acids such as tolueneoxysulfinic acid and phenoxysulfinic acid; xii) phosphoric acid $H_3PO_4$; xiii) acetic acid $CH_3C(O)$—OH; xiv) triflic acid $CF_3SO_3H$; and xv) tetrafluoroboric acid $HBF_4$;

the term "anionic counterion" means an anion or an anionic group derived from an organic or mineral acid which counterbalances the cationic charge of the dye; more particularly, the anionic counterion is chosen from: i) halides such as chloride or bromide; ii) nitrates; iii) sulfonates, including $C_1$-$C_6$ alkylsulfonates: Alk-S(O)$_2$O$^-$ such as methylsulfonate or mesylate and ethylsulfonate; iv) arylsulfonates: Ar—S(O)$_2$O$^-$ such as benzenesulfonate and toluenesulfonate or tosylate; v) carboxylates Alk-C(O)—OH with Alk representing a ($C_1$-$C_6$) alkyl group optionally substituted with one or more hydroxyl or carboxylate groups such as citrate; vi) succinate; vii) tartrate; viii) lactate; ix) alkyl sulfates: Alk-O—S(O)O$^-$ such as methyl sulfate and ethyl sulfate; x) aryl sulfates: Ar—O—S(O)O$^-$ such as benzene sulfate and toluene sulfate; xi) alkoxy sulfates: Alk—O—S(O)$_2$O$^-$ such as methoxy sulfate and ethoxy sulfate; xii) aryloxy sulfates: Ar—O—S(O)$_2$O$^-$, xiii) phosphates O=P(OH)$_2$—O$^-$, O=P(O$^-$)$_2$—OH O=P(O$^-$)$_3$, HO$_4$[P(O)(O$^-$)]$_w$—P(O)(O$^-$)$_2$ with w being an integer; xiv) acetate; xv) triflate; and xvi) borates such as tetrafluoroborate, and xvii) disulfate (O=)$_2$S(O$^-$)$_2$ or SO$_4^{2-}$ and monosulfate HSO$_4^-$;

As previously explained, the process according to the invention uses i) at least one thiol-based reducing agent and ii) at least one organic solvent, it being understood that the composition(s) containing said thiol-based reducing agent(s) are acidic; preferably said composition(s) have a pH between 1 and 5 inclusive, preferably between 2.5 and 4 inclusive.

The thiol-based reducing agent(s) present in composition (A) used according to the invention are chosen from organic compounds comprising one or more mercapto (—SH or —S—) groups, or disulfide (—S—S—) groups, preferably —SH groups and at least one other function chosen from carboxylic acid, amine, amide, ester and alcohol functions, and mixtures thereof.

According to a particular embodiment of the invention, the reducing agent(s) used in the invention are chosen from those of formulae i-1 and i-2, and also the organic or mineral acid or base salts thereof, optical isomers thereof and tautomers thereof, and the solvates such as hydrates:

in which formulae i-1 and i-2:
R represents:
  linear or branched (C$_1$-C$_8$)alkyl, preferably (C$_1$-C$_6$) alkyl,
    a) optionally substituted, preferably substituted, with one or more groups chosen from carboxy C(O) OH, (di)(C$_1$-C$_4$)(alkyl)amino, hydroxyl —OH and thiol —SH,
    and/or
    b) optionally interrupted with one or more heteroatoms or groups chosen from —O—, —S—, N(R''')— wherein R''' represents a hydrogen atom or a linear or branched (C$_1$-C$_6$)alkyl group, C(O) or combinations thereof such as —O—C(O)—, —C(O)—O—, —N(R''')—C(O)— or —C(O)—N (R''')—;
  (hetero)aryl optionally substituted in particular with one or more hydroxyl, thiol or carboxy groups;
R' and R'', which may be identical or different, represent a (C$_1$-C$_8$)alkyl group, preferably (C$_1$-C$_6$)alkyl group, substituted with one or more groups chosen from hydroxyl, thiol and carboxy;
  or else R' and R'' form, together with the sulfur atom which bears them, a 5- to 7-membered heterocyclic group, which is preferably saturated, which comprises from 1 to 3 heteroatoms, and which is optionally substituted (in particular with one or more (C$_1$-C$_6$)alkyl groups optionally substituted with one or more hydroxyl, thiol or carboxy groups), more preferentially the heterocyclic group is a dithiolane group optionally substituted with a (C$_1$-C$_6$)alkyl group optionally substituted with one or more carboxy groups.

According to one particular embodiment of the invention, the reducing agents are of formula i-1, in particular those for which R represents a linear or branched (C$_1$-C$_8$)alkyl group, preferably (C$_1$-C$_6$)alkyl group, substituted with one or more groups chosen from carboxyl C(O)OH, amino, hydroxyl —OH, and thiol —SH;

and/or optionally interrupted with one or more heteroatoms or groups chosen from —O—, —N(R''')— wherein R''' represents a hydrogen atom or a linear or branched (C$_1$-C$_6$) alkyl group, C(O) or combinations thereof such as —O—C(O)—, —C(O)—O—, —N(R''')—C(O)— or —C(O)—N (R''')—. Preferably, R represents a linear or branched, uninterrupted (C$_1$-C$_8$)alkyl group, preferably (C$_1$-C$_6$)alkyl group.

According to another particular embodiment of the invention, the reducing agents are of formula i-1 for which R represents:
  a phenyl group optionally substituted with one or more hydroxyl, thiol or carboxy groups; or
  a 5- to 10-membered and preferably 9- or 10-membered bicyclic heteroaryl, comprising from 1 to 4 heteroatoms chosen from O, S or N, preferably N, optionally substituted with one or more hydroxyl or thiol groups.

According to another particular embodiment of the invention, the reducing agents are of formula i-2, in particular those for which R' and R'', which may be identical or different, represent a (C1-C8)alkyl group, preferably (C1-C6)alkyl group, substituted with one or more groups chosen from hydroxyl, thiol and carboxy.

According to another particular embodiment of the invention, the reducing agents are of formula i-2, in particular those for which R' and R'' form, together with the sulfur atom which bears them, a 5- to 7-membered heterocyclic group, which is preferably saturated, which comprises from 1 to 3 heteroatoms, and which is optionally substituted with one or more (C$_1$-C$_6$)alkyl groups optionally substituted with one or more hydroxyl, thiol or carboxy groups, more preferentially the heterocyclic group is a dithiolane group optionally substituted with a (C$_1$-C$_6$)alkyl group optionally substituted with one or more hydroxyl, thiol or carboxy groups.

Preferably, the reducing agent(s) comprising at least one mercapto or disulfide group of the invention are chosen from thioglycolic acid, thiolactic acid or 2-mercaptopropionic acid, cysteine, cysteamine, homocysteine, glutathione, thioglycerol, thiomalic acid, 3-mercaptopropionic acid, thiodiglycol, 2-mercaptoethanol, dithiothreitol, thioxanthine, thiosalicylic acid, thiodiglycolic acid, lipoic acid, N-acetylcysteine, and thioglycolic or thiolactic acid esters and amides, in particular glyceryl monothioglyco late, and mixtures of these compounds.

The thiol-based reducing agent(s) as defined previously may be used especially in the form of salts, in particular alkali metal salts such as sodium and potassium salts, alkaline-earth metal salts, for example magnesium and calcium salts, ammonium salts, amine salts and amino alcohol salts. Ammonium thioglycolate may thus be used as thiol.

Particularly preferably, the thiol-based reducing agent(s) are chosen from thioglycolic acid and salts thereof, thiolactic acid and salts thereof, cysteamine and salts thereof, and mixtures thereof.

Even more preferentially, the thiol-based reducing agent(s) are chosen from thioglycolic acid and thiolactic acid.

The thiol-based reducing agent(s) included in composition (A) according to the invention are preferably present in an amount ranging from 0.02% to 15% by weight, preferably from 0.1% to 10%, and even more preferentially from 0.5% to 2% by weight, relative to the total weight of said composition.

The pH of composition (A) and/or (B) according to the invention may be adjusted to the desired value by means of basifying agents or acidifying agents that are usually used.

The organic alkaline agent(s) are preferably chosen from alkanolamines, in particular mono-, di- or tri-hydroxy($C_1$-$C_6$)alkylamines, such as triethanolamine, oxyethylenated and/or oxypropylenated ethylenediamines, amino acids, the polyamines of formula (VIII) below, and mixtures thereof:

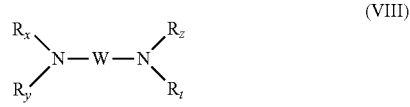

(VIII)

in which formula (VIII) W is a divalent $C_1$-$C_6$ alkylene radical optionally substituted with one or more hydroxyl groups or a $C_1$-$C_6$ alkyl radical, and/or optionally interrupted with one or more heteroatoms such as O, or $NR_u$; $R_x$, $R_y$, $R_z$, $R_t$ and $R_u$, which may be identical or different, represent a hydrogen atom or a $C_1$-$C_6$ alkyl, $C_1$-$C_6$ hydroxyalkyl or $C_1$-$C_6$ aminoalkyl radical.

Examples of amines of formula (VIII) that may be mentioned include 1,3-diaminopropane, 1,3-diamino-2-propanol, spermine and spermidine.

The term "alkanolamine" means an organic amine comprising a primary, secondary or tertiary amine function, and one or more linear or branched $C_1$ to $C_8$ alkyl groups bearing one or more hydroxyl radicals.

Organic amines chosen from alkanolamines such as monoalkanolamines, dialkanolamines or trialkanolamines comprising one to three identical or different $C_1$ to $C_4$ hydroxyalkyl radicals are in particular suitable for use in the invention.

Among the compounds of this type, mention may be made of monoethanolamine (MEA), diethanolamine, triethanolamine, monoisopropanolamine, diisopropanolamine, N,N-dimethylethanolamine, 2-amino-2-methyl-1-propanol, triisopropanolamine, 2-amino-2-methyl-1,3-propanediol, 3-amino-1,2-propanediol, 3-dimethylamino-1,2-propanediol and tris(hydroxymethyl)aminomethane.

More particularly, the amino acids that may be used are of natural or synthetic origin, in their L, D or racemic form, and comprise at least one acid function chosen more particularly from carboxylic acid, sulfonic acid, phosphonic acid and phosphoric acid functions. The amino acids may be in neutral or ionic form.

Among the basifying agents, mention may more particularly be made of aqueous ammonia, alkanolamines, and mineral or organic hydroxides.

Among the acidifying agents, mention may be made of i) hydrochloric acid HCl, ii) hydrobromic acid HBr, iii) sulfuric acid $H_2SO_4$, iv) alkylsulfonic acids: Alk-$S(O)_2OH$, such as methanesulfonic acid and ethanesulfonic acid; v) arylsulfonic acids: Ar—$S(O)_2OH$, such as benzenesulfonic acid and toluenesulfonic acid; vi) (poly)hydroxylated carboxylic acids, such as citric acid, succinic acid, tartaric acid or lactic acid, vii) alkoxysulfinic acids: Alk-O—S(O)—OH, such as methoxysulfinic acid and ethoxysulfinic acid; viii) aryloxysulfinic acids, such as tolueneoxysulfinic acid and phenoxysulfinic acid; ix) phosphoric acid $H_3PO_4$; x) acetic acid $CH_3C(O)$—OH; xi) triflic acid $CF_3SO_3H$ and xii) tetrafluoroboric acid $HBF_4$; more particularly, the mineral or organic acids used to acidify the composition(s) are chosen from hydrochloric acid, orthophosphoric acid, sulfuric acid, carboxylic acids, for instance acetic acid, tartaric acid, citric acid and lactic acid, and sulfonic acids.

The concentration of pH-adjusting agent(s) is in particular adjusted according to the pH of 1 to 5, preferentially 2.5 to 4, desired for the composition(s) containing the thiol-based reducing agent(s).

The organic solvent(s) of the invention are chosen from polar protic and aprotic solvents.

According to a particular embodiment of the invention, the polar solvents are chosen from polar aprotic solvents. Preferably, the polar aprotic solvents are solvents comprising one or more ester or carbonate or ketone or ether functions.

For the purposes of the invention, the term "polar solvent" means a solvent constituted of molecules with a dipole moment of greater than 1D (1 debye). In particular, the polar solvents according to the invention preferably comprise at least one heteroatom such as oxygen.

The term "polar protic solvent" means a polar solvent which also contains at least one hydrogen atom that is capable of participating in hydrogen bonding. In particular, the protic solvents according to the invention contain at least one hydrogen atom bonded to a heteroatom.

The term "polar aprotic solvent" means a polar solvent which does not contain any hydrogen atoms that are capable of participating in hydrogen bonding.

Preferably, the polar protic and aprotic solvent(s) are chosen from:

(b1) monoalcohols comprising a hydroxyl group and a $C_1$-$C_6$ and preferably $C_1$-$C_4$ alkyl group such as methyl, ethyl or (iso)propyl;

(b2) monoalcohols comprising a hydroxyl group and an aryl group, preferably phenyl such as phenol;

(b3) polyols comprising from 2 to 30 hydroxyl groups and a $C_2$-$C_8$ alkyl group, preferably a $C_2$-$C_4$ alkyl group;

(b4) polyols comprising from 2 to 10 hydroxyl groups and an aryl group, these polyols being different from the meta-hydroxyphenol derivatives as defined below;

(b5) esters of $C_1$-$C_{30}$ acids and of monoalcohols (b1), (b2) or of polyols (b3) or (b4), preferably esters of an in particular $C_{12}$-$C_{20}$ fatty acid and of $C_1$-$C_6$ monoalcohols, such as isopropyl myristate; these esters may be of carbonic acid, such as propylene carbonate;

(b6) ketones such as R—C(=O)—R', with R and R', which may be identical or different, representing a linear or branched $C_1$-$C_{30}$, preferably $C_1$-$C_6$ and in particular $C_1$-$C_4$ alkyl group, such as acetone or methyl ethyl ketone;

(b7) ethers such as R—O—R' with R and R' as defined previously, preferably $C_1$-$C_6$, in particular $C_1$-$C_4$, such as diethyl ether, and mixtures thereof.

More preferentially, the polar solvents of the invention are chosen from groups (b1), (b3), (b4) and (b5).

The term "monoalcohol" means an organic compound comprising only one "hydroxyl" (—OH) group; the organic compound may be a cyclic or linear or branched or acyclic aliphatic compound.

Advantageously, said monoalcohol(s) comprise from 2 to 4 carbon atoms.

Preferably, said monoalcohol(s) are chosen from ethanol, propanol, isopropanol and butanol, and a mixture of these compounds, and preferably said monoalcohol(s) are chosen from ethanol and isopropanol, and a mixture of these compounds, and more preferentially said monoalcohol is ethanol.

When they are present in the composition, the monoalcohols are in an amount between 1% and 60% inclusive, preferably between 10% and 50% and more preferentially between 20% and 50% by weight relative to the total weight of the composition.

The term "polyol" means an organic compound comprising at least two hydroxyl (—OH) groups, borne by different carbon atoms, this compound possibly being a cyclic or linear or branched or acyclic aliphatic compound.

More particularly, the polyol(s) that may be used according to the invention comprise from 2 to 30 hydroxyl groups, more preferentially from 2 to 10 hydroxyl groups and even more preferentially from 2 to 3 hydroxyl groups.

The polyol(s) that may be used according to the invention generally comprise at least three carbon atoms.

Preferably, said polyol(s) that may be used according to the invention are chosen from polyols comprising at least three carbon atoms and ethylene glycol, and preferably from propylene glycol, 1,3-propanediol, 1,3-butylene glycol, 1,2-pentanediol, dipropylene glycol, hexylene glycol, pentylene glycol, glycerol and ethylene glycol, and a mixture of these compounds, and more preferentially from propylene glycol and 1,3-propanediol, and a mixture of these compounds.

Preferably, these solvents are protic solvents chosen from alcohols and polyols, preferably with a boiling point of greater than 160° C., such as propylene glycol, or glycerol, or aprotic solvents bearing an ester function, such as isopropyl myristate.

According to a preferred embodiment of the invention, the solvent used in the process of the invention is used pure, not as a mixture with other polar organic solvents. Preferentially, said polar organic solvent is the only organic solvent present in composition (B) of the process of the invention.

Preferentially, the organic solvent(s) represent from 30% to 100% by weight of composition (B) and preferably from 60% to 100% by weight relative to the total weight of composition (B) containing them.

In a preferred embodiment, the process according to the invention preferably comprises a step o) of using a composition (C) containing one or more non-thiol-based reducing agents after step i) and/or ii) and before the heat treatment step iii).

According to a particular embodiment of the invention, the non-thiol-based reducing agent(s) present in composition (C) according to the invention are chosen from ortho-diphenol derivatives with reducing properties. In a manner known per se, the term "ortho-diphenol" denotes compounds comprising at least one aromatic ring, preferably a benzene ring, comprising at least two hydroxyl (OH) groups borne by two adjacent carbon atoms of the aromatic ring which in addition do not comprise a mercapto or disulfide group.

The aromatic ring may more particularly be a fused aryl or fused heteroaromatic ring, i.e. optionally comprising one or more heteroatoms, such as benzene, naphthalene, tetrahydronaphthalene, indane, indene, anthracene, phenanthrene, isoindole, indoline, isoindoline, benzofuran, dihydrobenzo furan, chroman, isochroman, chromene, isochromene, quinoline, tetrahydroquinoline and isoquinoline, said aromatic ring comprising at least two hydroxyl groups borne by two adjacent carbon atoms of the aromatic ring. Preferentially, the aromatic ring of the ortho-diphenol derivatives according to the invention is a benzene ring.

The term "fused ring" means that at least two saturated or unsaturated and heterocyclic or non-heterocyclic rings have a common bond, i.e. that at least one ring is joined side by side with another ring.

The ortho-diphenols according to the invention may or may not be salified. They may also be in aglycone form (without bonded sugars) or in the form of glycosylated compounds.

More particularly, the ortho-diphenol derivative represents a compound of formula (I), or an oligomer thereof, in salified or non-salified form:

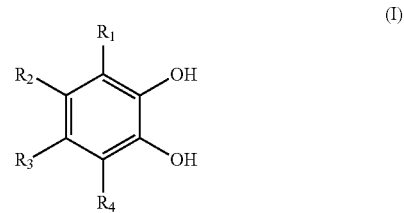

(I)

in which formula (I) the substituents:
$R_1$ to $R_4$, which may be identical or different, represent:
a hydrogen atom,
a halogen atom,
a hydroxyl radical,
a carboxyl radical;
an alkyl carboxylate or alkoxycarbonyl radical,
an optionally substituted amino radical,
an optionally substituted and linear or branched alkyl radical,
an optionally substituted and linear or branched alkenyl radical,
an optionally substituted cycloalkyl radical,
an alkoxy radical,
an alkoxyalkyl radical,
an alkoxyaryl radical, the aryl group possibly being optionally substituted,
an aryl radical,
a substituted aryl radical,
a saturated or unsaturated heterocyclic radical carrying or not carrying a cationic or anionic charge, optionally substituted and/or optionally fused with an aromatic ring, preferably a benzene ring, said aromatic ring being optionally substituted, in particular with one or more hydroxyl or glycosyloxy groups,
a radical containing one or more silicon atoms,
or two of the substituents carried by two adjacent carbon atoms $R_1$-$R_2$, $R_2$-$R_3$ or $R_3$-$R_4$ form, together with the carbon atoms carrying them, a saturated or unsaturated and aromatic or non-aromatic ring, optionally comprising one or more heteroatoms and optionally fused with one or more saturated or unsaturated rings optionally comprising one or more heteroatoms. Particularly, $R_1$ to $R_4$ together form from one to four rings.

A specific embodiment of the invention relates to ortho-diphenol derivatives of formula (I), two adjacent substituents $R_1$-$R_2$, $R_2$-$R_3$ or $R_3$-$R_4$ of which cannot form, with the carbon atoms which carry them, a pyrrolyl radical. More particularly, $R_2$ and $R_3$ cannot form a pyrrolyl radical fused to the benzene ring bearing the two hydroxyls.

The ortho-diphenols of use in the process of the invention can be natural or synthetic. The natural ortho-diphenols include the compounds which may be present in nature and which are reproduced by chemical (semi)synthesis.

The salts of the ortho-diphenols of the invention can be salts of acids or of bases. The acids may be mineral or organic. Preferably, the acid is hydrochloric acid, which results in chlorides.

The bases may be mineral or organic. In particular, the bases are alkaline hydroxides, such as sodium hydroxide, which results in sodium salts.

According to one particular embodiment of the invention, the composition(s) comprise as ingredient one or more synthetic ortho-diphenol derivatives that do not exist in nature.

According to another preferred embodiment of the invention, the process for curl-relaxing and/or straightening keratin fibres uses, as non-thiol-based agent, one or more natural ortho-diphenol derivatives.

More particularly, the ortho-diphenols that may be used in the process of the invention are in particular:
flavanols, such as catechin and epicatechin gallate,
flavonols, such as quercetin,
anthocyanidins, such as cyanidin, delphinidin or petunidin,
anthocyanins or anthocyans, for instance myrtillin,
ortho-hydroxybenzoates, for example gallic acid salts,
flavones, such as luteolin,
hydroxystilbenes, for example 3,3',4,5'-tetrahydroxystilbene, optionally oxylated (for example glucosylated),
3,4-dihydroxyphenylalanine and the derivatives thereof,
2,3-dihydroxyphenylalanine and the derivatives thereof,
4,5-dihydroxyphenylalanine and the derivatives thereof,
dihydroxycinnamates, such as caffeic acid and chlorogenic acid,
ortho-polyhydroxycoumarins,
ortho-polyhydroxyisocoumarins,
ortho-polyhydroxycoumarones,
ortho-polyhydroxyisocoumarones,
ortho-polyhydroxychalcones,
ortho-polyhydroxychromones,
ortho-polyhydroxyquinones,
ortho-polyhydroxyxanthones,
1,2-dihydroxybenzene and the derivatives thereof,
1,2,4-trihydroxybenzene and the derivatives thereof,
1,2,3-trihydroxybenzene and the derivatives thereof,
2,4,5-trihydroxytoluene and the derivatives thereof,
proanthocyanidins and especially the proanthocyanidins A1, A2, B1, B2, B3 and C1,
proanthocyanins,
tannic acid,
ellagic acid,
and mixtures of the preceding compounds.

When the dye precursors have D and L forms, the two forms may be used in the compositions according to the invention, as may the racemic mixtures.

According to one embodiment, the natural ortho-diphenols result from extracts of animals, bacteria, fungi, algae or plants, used in their entirety or partially. In particular as regards plants, the extracts are derived from plants or plant parts, such as fruit, including citrus fruit, vegetables, trees or shrubs. Use may also be made of mixtures of these extracts, which are rich in ortho-diphenols as defined above.

Preferably, the natural ortho-diphenols of the invention are derived from plants or plant parts.

The extracts are obtained by extraction of various plant parts, for instance the root, the wood, the bark, the leaf, the flower, the fruit, the seed, the pod or the peel.

Use may also be made of mixtures of plant extracts.

According to a specific embodiment of the invention, the ortho-diphenol derivative(s) are natural extracts rich in ortho-diphenols. According to a preferred form, the ortho-diphenol derivative(s) are solely natural extracts.

The natural extracts according to the invention may be in the form of powders or liquids. Preferably, the extracts of the invention are provided in the form of powders.

According to a particular embodiment of the invention, the non-thiol-based reducing agent(s) present in composition (C) according to the invention are chosen from meta-hydroxyphenol derivatives, also known as resorcinols, with reducing properties. In a manner known per se, the term "resorcinols" denotes compounds which comprise at least one aromatic ring, preferably a benzene ring, comprising at least two hydroxyl (OH) groups borne by two carbon atoms which are in the meta position relative to each other, and which also do not comprise any mercapto or disulfide groups.

The aromatic ring may more particularly be a fused aryl or fused heteroaromatic ring, i.e. optionally comprising one or more heteroatoms, such as benzene, naphthalene, tetrahydronaphthalene, indane, indene, anthracene, phenanthrene, isoindole, indo line, isoindoline, benzo furan, dihydrobenzo furan, chroman, isochroman, chromene, isochromene, quinoline, tetrahydroquinoline and isoquinoline, said aromatic ring comprising at least two hydroxyl groups borne by two carbon atoms which are in the meta position relative to each other. Preferentially, the aromatic ring of the resorcinol derivatives according to the invention is a benzene ring.

According to a more particular embodiment of the invention, the non-thiol-based reducing agent(s) present in the composition(s) used according to the invention are chosen from the meta-hydroxyphenol derivatives of formula (II), and also the organic or mineral acid or base salts thereof, and the solvates thereof such as hydrates:

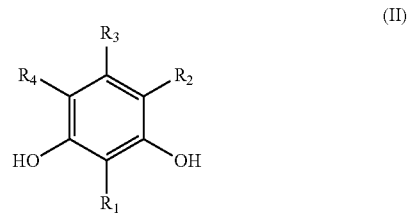

(II)

in which formula (II) the substituents:
$R_1$, $R_2$ and $R_4$, which may be identical or different, represent:
a hydrogen atom,
a halogen atom,
a carboxyl radical,
an alkyl carboxylate or alkoxycarbonyl radical,
an optionally substituted amino radical,
an optionally substituted and linear or branched alkyl radical,
an optionally substituted and linear or branched alkenyl radical,
an optionally substituted cycloalkyl radical,
an alkylcarbonyl radical,
a carboxaldehyde radical,
an alkoxy radical,
an alkoxyalkyl radical,
an alkoxyaryl radical, the aryl group possibly being optionally substituted, an arylalkylcarbonyl radical of which the aryl group, particularly phenyl group, is optionally substituted, preferably with one or more hydroxyl groups, an aryl radical, a substituted aryl radical, a saturated or unsaturated heterocyclic radical optionally bearing a cationic or anionic charge, optionally substituted and/or optionally fused with an aromatic ring, preferably a benzene ring, said aromatic ring being optionally substituted, in particular with one or more hydroxyl or glycosyloxy groups, a radical containing one or more silicon atoms, $R_3$ represents:

a hydrogen atom, a halogen atom, a hydroxyl radical, a carboxyl radical, an alkyl carboxylate or alkoxycarbonyl radical, an optionally substituted amino radical, an optionally substituted and linear or branched alkyl radical, a linear or branched alkenyl radical which is optionally substituted, in particular with a phenyl group which is preferably optionally substituted with one or more (di)($C_1$-$C_4$)(alkyl)amino or hydroxyl groups, an optionally substituted cycloalkyl radical, an alkylcarbonyl radical, a carboxaldehyde radical, an alkoxy radical, an alkoxyalkyl radical, an alkoxyaryl radical, the aryl group possibly being optionally substituted, an aryl radical, a substituted aryl radical, a saturated or unsaturated heterocyclic radical optionally bearing a cationic or anionic charge, optionally substituted and/or optionally fused with an aromatic ring, preferably a benzene ring, said aromatic ring being optionally substituted, in particular with one or more hydroxyl or glycosyloxy groups, a radical containing one or more silicon atoms, or two of the substituents borne by two adjacent carbon atoms $R_2$-$R_3$ or $R_3$-$R_4$ form, together with the carbon atoms bearing them, a saturated or unsaturated, non-aromatic ring, optionally containing one or more heteroatoms and optionally fused with one or more saturated or unsaturated rings optionally containing one or more heteroatoms. Particularly, $R_2$ to $R_4$ together form from two to four rings.

More particularly, the non-thiol-based reducing agent(s) present in composition (C) according to the invention are chosen from the meta-hydroxyphenols of formula (II) in which the substituents:

$R_1$, $R_3$ and $R_4$, which may be identical or different, represent:

a hydrogen atom, a halogen atom, a carboxyl radical, an alkyl carboxylate or alkoxycarbonyl radical, an optionally substituted amino radical, an optionally substituted and linear or branched alkyl radical, a linear or branched alkenyl radical which is optionally substituted, in particular with a phenyl group which is preferably optionally substituted with one or more (di)($C_1$-$C_4$)(alkyl)amino or hydroxyl groups, an alkylcarbonyl radical, a carboxaldehyde radical, an alkoxy radical, and/or $R_2$ represents:

a hydrogen atom, a halogen atom, a hydroxyl radical, a carboxyl radical, an alkyl carboxylate or alkoxycarbonyl radical, an optionally substituted amino radical, a phenylalkylcarbonyl radical of which the phenyl group is optionally substituted, preferably with one or more hydroxyl groups, an optionally substituted and linear or branched alkyl radical, an optionally substituted and linear or branched alkenyl radical, an alkylcarbonyl radical, a carboxaldehyde radical, an alkoxy radical.

More particularly, the substituent $R_2$ in formula (II) represents a hydrogen atom or a ($C_1$-$C_6$)alkyl group, preferably a hydrogen atom.

According to a particular embodiment of the invention, the non-thiol-based reducing agent(s) present in the composition (C) according to the invention are chosen from the resorcinol derivatives of formula (II), and also the organic or mineral acid or base salts thereof, and the solvates thereof such as hydrates:

in which $R^1$ to $R^4$, which may be identical or different, represent a hydrogen or halogen atom, or a group chosen from:

optionally substituted ($C_1$-$C_{10}$)alkyl, in particular optionally substituted with at least one hydroxyl radical;

optionally substituted ($C_2$-$C_{10}$)alkenyl, in particular optionally substituted with at least one aryl group such as a phenyl group optionally substituted with one or more (di)($C_1$-$C_4$)(alkyl)amino or hydroxyl groups;

($C_1$-$C_{10}$)alkoxy;

carboxy —C(O)—OH or carboxylate —C(O)—O$^-$, M$^+$; with M$^+$ representing a cationic counterion such as an alkali metal or alkaline-earth metal, or an ammonium;

ester —C(O)—O—R$^5$ or —O—C(O)—R$^5$, with R$^5$ representing a ($C_1$-$C_{10}$)alkyl group, particularly —C(O)—O—R$^5$;

amido —C(O)—NR$^6$R$^7$ or —NR$^6$—C(O)—R$^7$ with R$^6$ and R$^7$, which may be identical or different, representing a hydrogen atom or a ($C_1$-$C_{10}$)alkyl group, particularly —C(O)—NH$_2$;

($C_1$-$C_{10}$)alkylcarbonyl;

hydroxyl; and amino —NR$^8$R$^9$, with R$^8$ and R$^9$, which may be identical or different, representing a hydrogen atom or a ($C_1$-$C_{10}$)alkyl group, particularly —NH$_2$.

In particular, in formula (II), $R_1$, $R_2$ and $R_4$ represent a hydrogen atom or an optionally substituted ($C_1$-$C_6$)alkyl group, preferably hydrogen, and/or $R_3$ represents a hydrogen atom or a linear or branched ($C_1$-$C_6$)alkyl or ($C_2$-$C_6$)alkenyl group, such as ethenyl, optionally substituted with an aryl group, such as a phenyl group, which is optionally substituted, preferably with one or more (di)($C_1$-$C_4$)(alkyl)amino or hydroxyl groups.

More preferentially, the non-thiol-based reducing agent(s) present in the composition(s) used according to the invention are chosen from the resorcinol derivatives of formula (II), in which $R_1$, $R_2$ and $R_4$ represent a hydrogen atom or a $(C_1-C_4)$alkyl group, preferably hydrogen, and $R_3$ represents a hydrogen atom or an Ar—CH=CH— group with Ar representing an aryl group, in particular a phenyl group, said aryl group being optionally substituted, preferably with one or more hydroxyl groups; in particular, said hydroxyl group(s) are substituted in the ortho or para position relative to the phenyl group.

Preferably, the meta-hydroxyphenols according to the invention do not comprise two hydroxyl groups borne by two adjacent carbons.

The meta-hydroxyphenols of the invention may be natural or synthetic. Among the natural meta-hydroxyphenols are included compounds that may be present in nature and that are reproduced by chemical (semi)synthesis. The salts of the meta-hydroxyphenols of the invention may be salts of acids or of bases. The acids may be mineral or organic. Preferably, the acid is hydrochloric acid, which results in chlorides. The bases may be mineral or organic. In particular, the bases are alkaline hydroxides, such as sodium hydroxide, which results in sodium salts.

According to a particular embodiment of the invention, the composition comprises, as ingredient a), one or more synthetic meta-hydroxyphenol derivatives that do not exist in nature.

According to one embodiment, the natural meta-hydroxyphenols are derived from extracts of animals, bacteria, fungi, algae, plants and fruits, used in their entirety or partially. In particular regarding plants, the extracts are derived from fruits, including citrus fruits, from vegetables, from trees and from shrubs. Use may also be made of mixtures of these extracts, which are rich in meta-hydroxyphenols as defined above.

According to a particular embodiment of the invention, the non-thiol-based reducing agent(s) present in composition (C) according to the invention are chosen from para-hydroxyphenol derivatives with reducing properties. In a manner known per se, the term "para-hydroxyphenol" denotes compounds which comprise at least one aromatic ring, preferably a benzene ring, comprising at least two hydroxyl (OH) groups borne by two adjacent carbon atoms which are in the para position relative to each other, and which also do not comprise any mercapto or disulfide groups.

According to a more particular embodiment of the invention, the non-thiol-based reducing agent(s) present in composition (C) are chosen from the para-hydroxyphenol derivatives of formula (III), and also the organic or mineral acid or base salts thereof, and the solvates thereof such as hydrates:

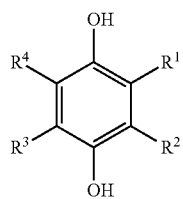

(III)

in which formula (III) $R^1$ to $R^4$, which may be identical or different, are as defined previously for formulae (I) and (II), and preferably represent a hydrogen atom or an optionally substituted $(C_1-C_4)$alkyl group, preferably hydrogen.

Preferentially, the non-thiol-based agent(s) are chosen from catechol, gallic acid, para-hydroxyphenol or resveratrol, it being understood that, when the aromatic ring of the ortho-diphenols, meta-hydroxyphenols or para-hydroxyphenols bear more than two hydroxyl groups (for example three, four, etc.), the compounds should be understood according to the following rule:

If three hydroxyl groups are adjacent on the aromatic ring: (position 1, 2, 3 for example), then said non-thiol-based reducing agent will be considered to be an ortho-diphenol.

If there are three hydroxyl groups, two of which are adjacent on the aromatic ring and one is opposite (positions 1, 2, 4 or 1, 2, 5), then said non-thiol-based reducing agent will be considered to be a para-hydroxyphenol.

If there are three hydroxyl groups, none of which is adjacent (position 1, 3, 5), then said non-thiol-based reducing agent will be considered to be a meta-hydroxyphenol.

Preferentially, the non-thiol-based reducing agent(s) represent from 1% to 10% by weight and preferably from 2% to 8% by weight relative to the total weight of composition (C) containing them.

When the process of the invention comprises step o) of applying composition (C), the weight ratio between the amount of thiol-based reducing agent(s) and the amount of non-thiol-based reducing agent(s) is between 0.01 and 10, particularly between 0.1 and 5 inclusive, and more preferentially between 0.2 and 1 inclusive.

In one embodiment, the pH of composition (C) is between 1 and 5 inclusive, preferably between 2.5 and 4.

In one embodiment, the pH of composition (A) is between 1 and 5 inclusive, preferably between 2.5 and 4.

In a particular embodiment of the invention, composition (C) comprising the non-thiol-based agent(s) is generally applied before and/or after composition (A) comprising the thiol-based agent(s), and preferably after composition (A). In other words, in this variant, the process according to the invention comprises step i) of applying composition (A), step o) of applying composition (C), step ii) of applying composition (B), and then iii) the heating step. This alternative is preferred.

In this preferred embodiment, the process of the invention preferably does not comprise a step of rinsing the keratin fibres between step i) and step o) before step ii) of applying composition (B).

According to one variant of the invention, the process according to the invention does not use para-hydroxyphenol derivatives as described above.

Consecutively according to this variant, the compositions of the invention used according to the process of the invention do not comprise parahydroxyphenol derivatives as described above.

According to a preferred embodiment, the composition(s) used according to the invention are non-dyeing, i.e. they do not comprise any direct dyeing or oxidation dyeing agents other than the non-thiol-based reducing agents when they are coloured.

Most particularly preferably in this embodiment, the process comprises:
  the application to the fibres of a composition (A) comprising said thiol-based agent(s) at a pH of between 1 and 5, and then
  an optional step of rinsing the fibres, and then
  the application to the fibres of a composition (C) comprising said non-thiol-based agent(s),
  the application to the fibres of a composition (B) comprising said organic solvent(s), and then a step of heat treatment of the fibres by means of a heating tool.

According to a particular embodiment of the invention, the composition(s) used in the process according to the invention may also comprise one or more nonionic, anionic, cationic, or amphoteric or zwitterionic surfactants.

Surfactants

The composition according to the present invention may optionally also comprise one or more surfactants.

The surfactant(s) that may be used in the composition according to the invention may be chosen from nonionic surfactants, cationic surfactants, anionic surfactants and amphoteric or zwitterionic surfactants, and mixtures thereof.

The composition according to the present invention may thus comprise one or more nonionic surfactants.

The nonionic surfactants that may be used are described, for example, in the *Handbook of Surfactants* by M. R. Porter, published by Blackie & Son (Glasgow and London), 1991, pages 116-178.

Examples of nonionic surfactants that may be mentioned include the following nonionic surfactants:

oxyalkylenated ($C_8$-$C_{24}$)alkylphenols;
saturated or unsaturated, linear or branched, oxyalkylenated or glycerolated $C_8$-$C_{40}$ alcohols, comprising one or two fatty chains;
saturated or unsaturated, linear or branched, oxyalkylenated $C_8$-$C_{30}$ fatty acid amides;
esters of saturated or unsaturated, linear or branched, $C_8$-$C_{30}$ acids and of polyethylene glycols;
preferably oxyethylenated esters of saturated or unsaturated, linear or branched, $C_8$-$C_{30}$ acids and of sorbitol;
esters of fatty acids and of sucrose;
($C_8$-$C_{30}$)alkyl(poly)glucosides, ($C_8$-$C_{30}$)alkenyl(poly)glucosides, which are optionally oxyalkylenated (0 to 10 oxyalkylene units) and comprising from 1 to 15 glucose units, ($C_8$-$C_{30}$)alkyl(poly)glucoside esters;
saturated or unsaturated oxyethylenated plant oils;
condensates of ethylene oxide and/or of propylene oxide;
N—($C_8$-$C_{30}$)alkylglucamine and N—($C_8$-$C_{30}$)acylmethylglucamine derivatives;
aldobionamides;
amine oxides;
oxyethylenated and/or oxypropylenated silicones;
and mixtures thereof.

The oxyalkylene units are more particularly oxyethylene or oxypropylene units, or a combination thereof, preferably oxyethylene units.

The number of moles of ethylene oxide and/or of propylene oxide preferably ranges from 1 to 250, more particularly from 2 to 100 and better still from 2 to 50; the number of moles of glycerol ranges in particular from 1 to 50 and better still from 1 to 10.

Advantageously, the nonionic surfactants according to the invention do not comprise any oxypropylene units.

As examples of glycerolated nonionic surfactants, use is preferably made of monoglycerolated or polyglycerolated $C_8$-$C_{40}$ alcohols, comprising from 1 to 50 mol of glycerol and preferably from 1 to 10 mol of glycerol.

Among the glycerolated alcohols, it is more particularly preferred to use the $C_8$/$C_{10}$ alcohol containing 1 mol of glycerol, the $C_{10}$/$C_{12}$ alcohol containing 1 mol of glycerol and the $C_{12}$ alcohol containing 1.5 mol of glycerol.

The nonionic surfactant(s) that may be used in the dye composition according to the invention are preferentially chosen from:

oxyethylenated $C_8$ to $C_{40}$ alcohols comprising from 1 to 100 mol of ethylene oxide, preferably from 2 to 50 and more particularly from 2 to 40 mol of ethylene oxide and comprising one or two fatty chains;
saturated or unsaturated oxyethylenated vegetable oils comprising from 1 to 100 and preferably from 2 to 50 mol of ethylene oxide;
($C_8$-$C_{30}$)alkyl(poly)glucosides, which are optionally oxyalkylenated (0 to 10 EO) and comprising 1 to 15 glucose units;
monoglycerolated or polyglycerolated $C_8$ to $C_{40}$ alcohols, comprising from 1 to 50 mol of glycerol and preferably from 1 to 10 mol of glycerol;
saturated or unsaturated, linear or branched, oxyalkylenated $C_8$-$C_{30}$ fatty acid amides;
esters of saturated or unsaturated, linear or branched, $C_8$-$C_{30}$ acids and of polyethylene glycols;
and mixtures thereof.

The composition according to the present invention may comprise one or more cationic surfactants.

The term "cationic surfactant" means a surfactant that is positively charged when it is contained in the compositions according to the invention. This surfactant may bear one or more positive permanent charges or may contain one or more cationizable functions in the compositions according to the invention.

The cationic surfactant(s) are preferably chosen from primary, secondary or tertiary fatty amines, which are optionally polyoxyalkylenated, or salts thereof, and quaternary ammonium salts, and mixtures thereof.

The fatty amines generally comprise at least one $C_8$ to $C_{30}$ hydrocarbon-based chain.

As quaternary ammonium salts, mention may especially be made of those corresponding to the general formula below:

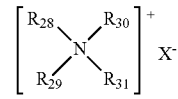

in which the groups $R_{28}$ to $R_{31}$, which may be identical or different, represent a linear or branched aliphatic group containing from 1 to 30 carbon atoms, or an aromatic group such as aryl or alkylaryl, at least one of the groups $R_{28}$ to $R_{31}$ denoting a group containing from 8 to 30 carbon atoms, preferably from 12 to 24 carbon atoms. The aliphatic groups may comprise heteroatoms especially such as oxygen, nitrogen, sulfur and halogens. The aliphatic groups are chosen, for example, from $C_1$-$C_{30}$ alkyl, $C_1$-$C_{30}$ alkoxy, polyoxy($C_2$-$C_6$)alkylene, $C_1$-$C_{30}$ alkylamide, ($C_{12}$-$C_{22}$)alkylamido($C_2$-$C_6$)alkyl, ($C_{12}$-$C_{22}$)alkyl acetate, and $C_1$-$C_{30}$ hydroxyalkyl groups, $X^-$ is an anion chosen from the group of halides, phosphates, acetates, lactates, ($C_1$-$C_4$)alkyl sulfates, and ($C_1$-$C_4$)alkyl- or ($C_1$-$C_4$)alkylarylsulfonates.

The anion $X^-$ is preferably a halide (chloride, bromide or iodide) or an alkyl sulfate, more particularly methyl sulfate. However, use may be made of methanesulfonate, phosphate, nitrate, tosylate, an anion derived from an organic acid, such as acetate or lactate, or any other anion that is compatible with the ammonium bearing an ester function.

The composition according to the present invention may comprise one or more anionic surfactants.

The term "anionic surfactant" means a surfactant comprising, as ionic or ionizable groups, only anionic groups. These anionic groups are preferably chosen from the groups —COOH, —COO⁻, $SO_3H$, —$SO_3^-$, —$OSO_3H$, —$OSO_3^-$, —$PO_2H_2$, —$PO_2H_-$, —$PO_2^{2-}$, —$P(OH)_2$, =$P(O)OH$, —$P(OH)O$—, =$P(O)O$—, =$POH$ and =$PO^-$, the anionic parts comprising a cationic counterion such as an alkali metal, an alkaline-earth metal or an ammonium.

The composition according to the present invention may comprise one or more amphoteric or zwitterionic surfactants.

In particular, the amphoteric or zwitterionic surfactant(s), which are preferably non-silicone, which may be used in the composition according to the present invention may in particular be derivatives of optionally quaternized, secondary or tertiary aliphatic amines, in which derivatives the aliphatic group is a linear or branched chain comprising from 8 to 22 carbon atoms, said amine derivatives containing at least one anionic group, for instance a carboxylate, sulfonate, sulfate, phosphate or phosphonate group.

The surfactants that may be used in the process according to the invention are preferably nonionic or cationic.

Preferably, when they are present, the surfactant(s) represent from 0.1% to 20% by weight and better still from 1% to 10% by weight relative to the total weight of each composition containing them.

The composition(s) that may be used in the process according to the invention generally comprise water, which typically represents from 10% to 90% by weight, preferably from 10% to 80% by weight, preferably from 10% to 70% by weight, relative to the total weight of each composition.

The compositions that may be used in the process according to the invention may also contain cosmetically acceptable organic solvents other than those contained in composition (B), more particularly including alcohols such as ethyl alcohol, isopropyl alcohol, benzyl alcohol and phenylethyl alcohol, or polyols or polyol ethers, for instance ethylene glycol monomethyl, monoethyl and monobutyl ethers, propylene glycol or ethers thereof, for instance propylene glycol monomethyl ether, butylene glycol, dipropylene glycol, and also diethylene glycol alkyl ethers, for instance diethylene glycol monoethyl ether or monobutyl ether.

The solvents may then represent from 0.5% to 20% by weight and preferably from 2% to 10% by weight relative to the total weight of each composition containing them.

The compositions used according to the invention may also comprise one or more cosmetic adjuvants other than the compounds described previously.

For example, they may comprise one or more standard additive(s) that are well known in the art, such as linear or cyclic, volatile or non-volatile silicones, cationic, nonionic, anionic or amphoteric polymers, peptides and derivatives thereof, protein hydrolysates, waxes, agents for preventing hair loss, vitamins and provitamins including panthenol, sunscreens, mineral or organic pigments, sequestrants, plasticizers, solubilizers, mineral or organic thickeners, antioxidants, nacreous agents, fragrances and preserving agents.

Needless to say, a person skilled in the art will take care to select this or these optional additional compounds such that the advantageous properties intrinsically associated with the compositions used according to the invention are not, or are not substantially, adversely affected by the envisaged addition(s).

The above additives may generally be present in an amount, for each of them, of between 0 and 20% by weight relative to the total weight of the composition containing them.

A person skilled in the art can choose the appropriate presentation form for the compositions according to the invention, and also the methods for preparing them, on the basis of his general knowledge, taking into account first the nature of the constituents used, in particular their solubility in the support, and secondly the application envisaged for the composition. Thus, the composition(s) according to the invention may be in the form of a suspension or a dispersion, in particular of oil-in-water by means of vesicles; an optionally thickened or even gelled oily solution; an oil-in-water, water-in-oil or multiple emulsion; a gel or a foam; an oily or emulsified gel; a dispersion of vesicles, in particular lipid vesicles; a two-phase or multiphase lotion; a spray. These compositions may have the appearance of a lotion, a cream, a salve, a soft paste, an ointment, a solid that has been cast or moulded and in particular as a stick or in a dish, or a compacted solid.

The compositions used in the process according to the invention may thus be in any form that is compatible with application to keratin fibres, for example in the form of a wax, a paste, a more or less fluid or thick cream, a gel, a foam, a spray or a lotion.

The compositions described previously are applied to wet or dry keratin fibres, sequentially or simultaneously.

The compositions are usually left in place on the fibres for a time generally ranging from 1 minute to 1 hour and preferably from 5 minutes to 30 minutes for each composition.

As described previously, the process according to the invention comprises a step of heat treatment of the fibres by means of a heating tool.

This heat treatment step is generally performed following the application of the composition(s) described above, optionally after removal thereof by rinsing.

Preferably, the heating tool is chosen from a hairstyling hood, a straightening iron (or flat iron), a hairdryer and an infrared-ray dispenser, and more preferentially the heating tool is a straightening iron. The iron is applied by successive separate strokes lasting a few seconds or by gradual movement or sliding along the locks.

The hair treatment step is generally performed at a temperature ranging from 30 to 250° C., preferably from 60 to 230° C. and more preferentially from 100 to 150° C.

According to a particular embodiment of the invention, the process for treating keratin fibres comprises, as heat treatment, a step of straightening/uncurling the keratin fibres by means of a heating tool chosen from irons and a steam iron, i.e. "irons" which comprise a device that emits steam and that applies this steam before, during or after the straightening/uncurling.

For the purposes of the present invention, the term "iron" means a device for heating keratin fibres by placing said fibres and the heating device in contact. The end of the iron which comes into contact with the keratin fibres generally has two flat surfaces. These two surfaces may be made of metal or of ceramic. In particular, these two surfaces may be smooth or crimped or curved.

According to a particular embodiment, the iron or the steam iron is at a temperature of between 65° C. and 250° C., particularly between 80° C. and 230° C., more particularly greater than or equal to 100° C. and preferentially between 100° C. and 190° C. Preferably, the heat treatment step of the process for treating keratin fibres is performed at a temperature ranging from 150° C. to 230° C., preferably ranging from 160° C. to 230° C., preferentially ranging from 160° C. to 210° C., especially ranging from 180° C. to 200° C.

As examples of irons that may be used in the straightening process according to the invention, mention may be made of any type of flat steam iron, and in particular, in a non-limiting manner, those described in U.S. Pat. Nos. 5,957,140 and 5,046,516.

The steam iron may be applied by successive separate strokes lasting a few seconds or by gradual movement or sliding along the locks of keratin fibres, especially of hair.

Preferably, the steam iron is applied in the process according to the invention by a continuous movement from the root to the end of the hair, in one or more passes, in particular in two to twenty passes. The duration of each pass of the steam iron may range from 2 seconds to 1 minute.

Advantageously, steam is applied to the keratin fibres, especially the hair, at a flow rate of less than 5 g/min, especially of between 1 and 4 g/min.

Steam may be applied using any device known per se for generating the amount of steam of use in the process of the invention. According to a particular embodiment, this machine is portable, i.e. the tank for generating steam is in contact with the part of the device comprising the steam-dispensing orifices.

The steam application step may be performed before, during or after the heating step, and preferably before.

Preferably, the step of straightening/relaxing the keratin fibres is performed for a time that may range from 2 seconds to 30 minutes, preferentially from 2 seconds to 20 minutes, better still from 2 seconds to 10 minutes, better still from 2 seconds to 5 minutes and even better still from 2 seconds to 2 minutes.

Preferably, step ii) is performed with a steampod steam straightening device.

The process according to the invention may also comprise an additional step of drying the keratin fibres, after the application steps i), optionally o) and ii), and before the heat treatment step iii). The drying step may be performed using a hairdryer or a drying hood or by drying in the open air. The drying step is advantageously performed at a temperature ranging from 20 to 70° C.

After the step of straightening/relaxing using the steam iron, the keratin fibres may be optionally rinsed with water or washed with a shampoo. The keratin fibres are subsequently optionally dried using a hairdryer or a drying hood or in the open air.

According to one embodiment, the process according to the invention is performed on natural keratin fibres, especially natural hair.

According to another embodiment, the process according to the invention is performed on keratin fibres, especially damaged hair. The term "damaged hair" means dry or coarse or brittle or split or limp hair.

The process of the invention is particularly performed on sensitized human keratin fibres, especially hair, such as bleached, relaxed or permanent-waved fibres.

The process according to the invention may be performed on keratin fibres, especially hair, which is wet or dry. Preferentially, the process is performed on natural keratin fibres.

After the application steps i) and ii) of the process of the invention, and before the heat treatment step iii) is performed, composition(s) A and/or B applied may be left on for a period ranging from 1 to 60 minutes, preferably ranging from 2 to 50 minutes, preferentially ranging from 5 to 45 minutes. The leave-on period may take place at a temperature ranging from 15° C. to 45° C., preferably at room temperature (25° C.).

The cosmetic composition which contains the thiol-based reducing agents, as described previously, is advantageously applied to the keratin fibres in an amount ranging from 0.1 to 10 grams and preferably from 0.2 to 5 grams of composition per gram of keratin fibres.

The cosmetic composition which contains the polar organic agents, as described previously, is advantageously applied to the keratin fibres in an amount ranging from 0.1 to 10 grams and preferably from 0.2 to 5 grams of composition per gram of keratin fibres.

The cosmetic composition which contains the non-thiol-based reducing agents, as described previously, is advantageously applied to the keratin fibres in an amount ranging from 0.1 to 10 grams and preferably from 0.2 to 5 grams of composition per gram of keratin fibres.

After application of the cosmetic composition(s) A and/or B to the keratin fibres, said fibres may be wrung out to remove the excess composition or washed with water or with a shampoo.

The treatment process according to the invention may be performed before, during and/or after an additional process of cosmetic treatment of the keratin fibres, such as a process for temporary curl relaxation (relaxing of curls with curlers, a crimping iron or a straightening iron) or a process for long-lasting curl relaxation (permanent-waving or uncurling) of the keratin fibres.

The process according to the invention may also comprise an additional step of partially predrying the hair fibres before the step of increasing the temperature, so as to prevent the evolution of large amounts of steam, which might burn the hairstylist's hands and the subject's scalp. This predrying step may be performed, for example, by means of a dryer or of a drying hood or else by drying in the open air.

Before and/or on conclusion of the process according to the invention, the keratin fibres may optionally be washed with a shampoo, followed by rinsing with water, before being dried or left to dry.

The process according to the invention may be repeated so as to increase the effects, until the desired level of straightening is obtained. However, and this constitutes an advantage of the present invention, from the very first implementation of the process according to the invention, including implementation without placing the hair under tension, a substantial reduction in the volume of the head of hair is observed. When the hair is curly, relaxation of the curls and/or better curl definition are also observed.

It is also found that the unpleasant odours that are given off during the straightening process, or that remain on the straightened hair, are reduced by means of performing the process according to the invention.

According to a preferred embodiment, the process is repeated several times, either consecutively or after a delay ranging from a few hours to a few days.

A subject of the present invention is also a kit that is suitable for performing the process of the invention. This kit comprises at least two compartments:
  a first compartment comprising an acidic composition (A) which comprises one or more thiol-based reducing agents, as defined above, preferably having a pH of between 1 and 5 inclusive, preferentially between 2.5 and 4,
  a second compartment comprising a composition (B) which comprises one or more organic solvents as defined above, and
  optionally, a third compartment comprising a composition (C) which comprises one or more non-thiol-based reducing agents, as defined above.

The compositions of this kit are packaged in separate compartments, which may be optionally accompanied by suitable identical or different application means, such as fine brushes, coarse brushes or sponges.

The abovementioned kit may also be equipped with means for dispensing the desired mixture on the hair, for instance the device described in patent FR 2 586 913.

The examples that follow illustrate the present invention, and should not in any way be considered as limiting the invention.

EXAMPLES

Example 1 a) Protocol for Preparing the Compositions Used in the Process of the Invention:

Thiolactic acid is tested comparatively in solution at 8% by weight in water at pH 3.5.

para-Hydroxyphenol is tested in solution at 5% by weight in water at pH 3.5.

Several polar solvents were tested according to the invention (composition (B))
  polar protic solvents, for instance propylene glycol, or glycerol,
  polar aprotic solvents bearing an ester function, for instance isopropyl myristate, and
  apolar aprotic solvents corresponding to the comparative, for instance isododecane.

The various solvents, propylene glycol, glycerol, isododecane or isopropyl myristate, are used pure at a rate of 2 g of solvent per gram of lock.

b) Protocol for Evaluating the Technical Effect (Stability, Performance During/After Application, Texture)

b1) Each composition prepared in the preceding preparation protocol a) was tested on natural and/or bleached locks according to straightening treatment protocols.

b2) Protocol for Brazilian straightening with a conventional iron:

The locks of keratin fibres were combed, and then were subjected to 10 successive blow drying passes, at position 2 (80° C.) of the hairdryer, with a medium-diameter round brush. Each of the locks was then separated into two. Each part was subjected to 10 passes with the straightening iron using a comb on each half, then ⅔ passes over all of it at 230° C.

The locks were then washed with a mild shampoo, and dried.

c) Sensory Results of the In Vitro Evaluation

The in vitro tests were performed with the various compositions so as to measure the protective effect of the tested solvent composition and its capacity to not overexpose the embrittled areas of the hair, such as the ends.

The protective effects of the various solvents in the straightening process of the invention are collated in the table below:

|  | | Protective effect | |
|---|---|---|---|
|  | Solvent tested | Solvent 1 protocol | Solvent 2 protocol |
| References | Control (thiol-based reducing agent) | – | – |
|  | Placebo | – | – |
| Apolar aprotic solvent (comparative) | Isododecane | – | – |

|  | | Protective effect | |
|---|---|---|---|
|  | Solvent tested | Solvent 1 protocol | Solvent 2 protocol |
| Polar protic solvent (invention) | Propylene glycol | +++ | +++ |
|  | Glycerol | ++ | ++ |
| Polar aprotic solvent bearing an ester function (invention) | Isopropyl myristate | +++ | +++ |

Each of the above properties was evaluated by experts, who attributed a score ranging from 1 to 4 according to the following scale:
  1—no effect (−)
  2—slight effect (+)
  3—pronounced effect (++)
  4—significant effect (+++)

The protocol used for the "Control" consists in applying a thiol-based reducing agent for 30 minutes, rinsing, blow-drying and treating with an iron at a temperature of 230° C.

The protocol named "solvent 1" consists in applying a thiol-based reducing agent for 30 minutes, rinsing, applying a solvent for 10 minutes, blow-drying and treating with an iron at a temperature of 230° C.

The protocol named "solvent 2" consists in applying a thiol-based reducing agent for 30 minutes, rinsing, applying a non-thiol-based reducing agent for 10 minutes, applying a solvent for 10 minutes, blow-drying and treating with an iron at a temperature of 230° C.

These tests on locks show that the protic solvents: propylene glycol, glycerol, and the aprotic solvent bearing an ester function: isopropyl myristate, make it possible to protect the sensitized areas of the hair while at the same time conserving the same straightening performance qualities, which is not possible with the use of aprotic solvents.

d) Examples of Compositions (A) According to the Invention

| Active agent | Water | Pure thiolactic acid (Aldrich) | 2-Amino-2-methyl-1-propanol | para-Hydroxy-phenol (Aldrich) | 0.1N HCl (Aldrich) |
|---|---|---|---|---|---|
| 8% Thiol-based reducing agent formula composition pH 3.5 | qs 100 g | 8.0 g | 3.0 g | — | — |
| 5% Non-thiol-based reducing agent formula composition pH 3.5 | qs 100 g | — | — | 5.0 g | 0.25 g |

Example 2

Preparation of the Compositions

Composition A1: Solution of thiolactic acid at 8% by weight at pH 3.5.

In a 150 ml flask 8 grams of thiolactic acid was added, then 50 grams of water was added and then 2-amino-2-methyl-1-propanol was added until a pH of the solution at 3.5 was obtained. It was then supplemented with water up to 100 grams and the final pH was checked (3.51).

Composition A2: Solution of thiolactic acid at 8% by weight at pH 8.5.

In a 150 ml flask 8 grams of thiolactic acid was added, then 50 grams of water was added and then 2-amino-2-methyl-1-propanol was added until a pH of the solution at 8.5 was obtained. It was then supplemented with water up to 100 grams and the final pH was checked (8.52).

Composition B: pure propylene glycol (or 1,2 propanediol).

Protocols

The following treatments were performed on natural Brazilian type locks (type IV).

Treatment 1 (Invention):

A 2.7 grams lock is placed flat on a sheet of aluminum foil on a lock plate at 27° C. 5.4 grams of composition A1 were gently deposited along the lock and then applied with a coloring brush so as to have a homogeneous treatment. It was then left for 30 minutes and then wrung with a paper and rinsed with water (10 passes between the fingers). 5.4 grams of composition B was then deposited along the lock (2 grams and then applied with a coloring brush to have a homogeneous treatment. It was then left for 10 minutes and then wrung with a paper. A blow-dry was then carried out at 80° C. (10 passes) and a hair straightening with straightening iron was carried out at 230° C. (10 passes in 6 seconds). A shampoo was then performed (0.4 gram per gram of hair). The lock was then allowed to air dry.

Treatment 2 (Comparative):

A 2.7 grams lock is placed flat on a sheet of aluminum foil on a lock plate at 27° C. 5.4 grams of composition A2 were gently deposited along the lock and then applied with a coloring brush so as to have a homogeneous treatment. It was then left for 30 minutes and then wrung with a paper and rinsed with water (10 passes between the fingers). 5.4 grams of composition B was then deposited along the lock (2 grams and then applied with a coloring brush to have a homogeneous treatment. It was then left for 10 minutes and then wrung with a paper. A blow-dry was then carried out at 80° C. (10 passes) and a hair straightening with straightening iron was carried out at 230° C. (10 passes in 6 seconds). A shampoo was then performed (0.4 gram per gram of hair). The lock was then allowed to air dry.

The length of the lock of each treatment was then measured by placing the lock on an A4 millimeter paper.

Results:

The enclosed figure shows:

on the left, the lock of hair treated according to treatment 1 as described previously (the composition containing one or more thiol-based reducing agents having a pH=3.51); and on the right, the lock of hair treated according to treatment 2 as described previously (the composition containing one or more thiol-based reducing agents having a pH=8.52).

Furthermore, the length of each lock of hair was measured. The following results were obtained:

Treatment 1:

Length: 25.9 cm,

Number of remaining ripples after treatment 1: one slight ripple.

Treatment 2:

Length: 25 cm,

Number of remaining ripples after treatment 2: three ripples are clearly visible.

The above results and the enclosed figure show that the process according to the invention (treatment 1) makes it possible to obtain a hair straightening that is significantly more efficient than that obtained with the comparative process (treatment 2).

The invention claimed is:

1. Process for straightening hair, comprising:
   i) the application to said fibers of an acidic composition (A), having a pH between 1 and 5 inclusive, and containing thiolactic acid in an amount ranging from 0.02% to 15% by weight relative to the total weight of composition (A);
   ii) the application to said hair of a distinct composition (B) consisting of propylene glycol, in an amount of 100% by weight relative to the total weight of composition (B); followed by
   iii) a step of heat treatment of the hair
   wherein the heat treatment step iii) is performed by a heating tool chosen from a hairstyling hood, a straightening iron, a hair dryer, an infrared-ray dispenser and wherein the heat treatment step is performed at a temperature ranging from 30 to 250° C.

* * * * *